(12) United States Patent
Flynn et al.

(10) Patent No.: US 8,206,854 B2
(45) Date of Patent: Jun. 26, 2012

(54) HYDROGEN ODORIZATION

(75) Inventors: Patrick J. Flynn, Coatesville, PA (US);
Michael J. Sprague, Edmonton (CA)

(73) Assignee: ENERSOL Inc., N.A.L.P., Fairfax, VA (US)

( * ) Notice: Subject to any disclaimer, the term of this patent is extended or adjusted under 35 U.S.C. 154(b) by 276 days.

(21) Appl. No.: 12/470,024

(22) Filed: May 21, 2009

(65) Prior Publication Data
US 2010/0171079 A1    Jul. 8, 2010

Related U.S. Application Data

(60) Provisional application No. 61/054,978, filed on May 21, 2008, provisional application No. 61/056,472, filed on May 28, 2008.

(51) Int. Cl.
*C01B 3/00* (2006.01)
*H01M 8/06* (2006.01)
(52) U.S. Cl. ............. 429/408; 206/0.6; 222/3; 252/372; 431/356
(58) Field of Classification Search .................. 252/372; 429/408; 431/356; 206/0.6; 222/3
See application file for complete search history.

(56) References Cited

U.S. PATENT DOCUMENTS

| | | | |
|---|---|---|---|
| 6,820,464 B2 | 11/2004 | Puri et al. | |
| 7,182,796 B2 | 2/2007 | Kato | |
| 7,229,831 B2 | 6/2007 | Puri | |
| 7,267,901 B2 | 9/2007 | Miura et al. | |
| 2004/0031314 A1 | 2/2004 | Flynn et al. | |
| 2004/0082488 A1 | 4/2004 | Duprey et al. | |
| 2004/0197919 A1* | 10/2004 | Herman et al. | 436/3 |
| 2006/0096158 A1 | 5/2006 | Robinson | |
| 2006/0211119 A1 | 9/2006 | Herman et al. | |

FOREIGN PATENT DOCUMENTS

| | | |
|---|---|---|
| WO | WO 2006/067111 | 6/2006 |
| WO | WO 2006/067113 | 6/2006 |
| WO | WO/2006/067115 | 6/2006 |

OTHER PUBLICATIONS

Pregassame, et al., "Hydrogen refueling station: filling control protocols development," WHEC/6 Jun. 13-16, 2006, Lyon France.

* cited by examiner

*Primary Examiner* — Wayne Langel
(74) *Attorney, Agent, or Firm* — Fox Rothschild LLP; Peter J. Butch, III; Robert N. Henrie, II (57) ABSTRACT

A composition comprising: hydrogen; and an oxygenate odorant; wherein the oxygenate odorant has a vapor pressure of about 0.002 psi. or greater at 25° C. and having a smell detectable at less than 1 ppm by a human nose; wherein the oxygenate odorant includes one or more carbonyl groups; and wherein the oxygenate odorant consists only of carbon, hydrogen and oxygen. The oxygenate odorants may be cyclic or acyclic.

40 Claims, 3 Drawing Sheets

FIG. 3

HYDROGEN ODORIZATION

PRIORITY DATA AND INCORPORATION BY REFERENCE

This application claims benefit of priority to U.S. Provisional Patent Application No. 61/054,978 filed May 21, 2008, entitled "Hydrogen Odorization" and to U.S. Provisional Patent Application No. 61/056,472 filed May 28, 2008, entitled "Hydrogen Odorization". Both of these applications are hereby incorporated by reference in their entirety.

BACKGROUND OF THE INVENTION

1. Field of the Invention

The present invention relates generally to gas leak detection by odorization to improve safety during transport, delivery, and end use. In particular, the invention relates to leak detection by odorization for gaseous fuels, most notably hydrogen fuel.

2. Background of the Technology

Hydrogen is considered by many to be the fuel of the future due to its high availability, very high calorific value, wide flammability limits and non-polluting nature. However, the highly combustible nature of hydrogen poses a great hazard creating a number of problems with its safety and handling. Therefore, leak detection in hydrogen systems is critical for any hydrogen application. Pure hydrogen is a colorless and odorless gas. There are many different types of mechanical 'hydrogen gas detectors', but as with any mechanical device, these detectors are also prone to mechanical failure. Even the most durable hydrogen sensors are too costly and cumbersome for automotive use. Existing sensors are too easily jostled, and their reactive metals, which include expensive noble-metals such as palladium, are ruined by contact with gases and particles that are common on the road. Considering the dangers associated with an extremely flammable gas like hydrogen, it becomes necessary to have an odorant for this fuel just as there are mercaptans for detecting natural gas leaks, accepted widely as a means of maintaining safety.

While gasoline, diesel, gasoline hybrid, and diesel hybrid vehicles are prevalent and electric and fuel cell vehicles are becoming more common in the transportation industry, vehicles do not currently incorporate hydrogen odorants or odorant removal systems. Some of the shortcomings and disadvantages associated with gasoline and diesel vehicles include pollution and dependency upon imported oil. Current electric vehicles, unfortunately, require a long battery charge time when not in operation. The main barrier to a widespread adoption of fuel cell vehicles is a lack of re-fueling infrastructure.

SUMMARY OF THE INVENTION

According to a first broad aspect, the present invention provides a composition comprising: hydrogen gas; and an oxygenate odorant; wherein the oxygenate odorant has a vapor pressure of about 0.002 psi or greater at 25° C. and 1 atm; wherein the oxygenate odorant has a smell detectable at less than 1 ppm by a human nose; wherein the oxygenate odorant includes one or more carbonyl groups; wherein the oxygenate odorant consists only of carbon, hydrogen and oxygen; and wherein the oxygenate odorant is a cyclic compound.

According to a second broad aspect, the present invention provides a composition comprising: hydrogen gas; and an oxygenate odorant; wherein the oxygenate odorant has a vapor pressure of about 0.002 psi or greater at 25° C. and 1 atm; wherein the oxygenate odorant has a smell detectable at less than 1 ppm by a human nose; wherein the oxygenate odorant includes one or more carbonyl groups; wherein the oxygenate odorant consists only of carbon, hydrogen and oxygen; and wherein the oxygenate odorant is a diketone having at least five carbon atoms.

According to a third broad aspect, the present invention provides a composition comprising: hydrogen gas; and an oxygenate odorant; wherein the oxygenate odorant has a vapor pressure of about 0.002 psi or greater at 25° C. and 1 atm; wherein the oxygenate odorant has a smell detectable at less than 1 ppm by a human nose; wherein the oxygenate odorant includes one or more carbonyl groups; wherein the oxygenate odorant consists only of carbon, hydrogen and oxygen; and wherein the oxygenate odorant is an alkyl vinyl ketone.

According to a fourth broad aspect, the present invention provides a composition comprising: hydrogen gas; and an oxygenate odorant; wherein the oxygenate odorant has a vapor pressure of about 0.002 psi or greater at 25° C. and 1 atm; wherein the oxygenate odorant has a smell detectable at less than 1 ppm by a human nose; wherein the oxygenate odorant includes one or more carbonyl groups; wherein the oxygenate odorant consists only of carbon, hydrogen and oxygen; and wherein the oxygenate odorant is an acyclic aldehyde.

According to a fifth broad aspect, the present invention provides a composition comprising: hydrogen gas; and an oxygenate odorant; wherein the oxygenate odorant has a vapor pressure of about 0.002 psi or greater at 25° C. and 1 atm; wherein the oxygenate odorant has a smell detectable at less than 1 ppm by a human nose; wherein the oxygenate odorant includes one or more carbonyl groups; wherein the oxygenate odorant consists only of carbon, hydrogen and oxygen; and wherein the oxygenate odorant is an alkyl formate.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "adsorption" refers to adhesion of molecules of a gas, liquid or dissoved substance to a surface.

For the purposes of the present invention, the term "butyrolactone" refers to any butyrolactone, including any butyrolactone having one or more alkyl and/or alkenyl groups on the ring of the butyrolactone. An example of a butyrolactone is γ-butyrolactone.

For the purposes of the present invention the term "container" refers to any type of container that may contain hydrogen or through which hydrogen may pass, including for example a metal container, a fuel cell, combustor, a pipe, etc.

For the purposes of the present invention, the term "convection zone" refers to the volumetric space by which the leak velocity controls hydrogen transport or hydrogen composition transport.

For the purposes of the present invention, the term "cyclohexanone" refers to cyclohexanone and any derivative of cyclohexanone including having one or more alkyl and/or alkenyl groups on the ring of cyclohexanone.

For the purposes of the present invention, the term "cyclohexenone" refers to any cyclohexenone, including any cyclohexenone having one or more alkyl and/or alkenyl groups on the ring of cyclohexenone. Examples of cyclohexenones include: 2-cylohex-2-en-1-one and 3-cyclohexen-1-one.

For the purposes of the present invention, the term "cyclohexanal compound" refers to cyclohexanal and any derivative of cyclopentaldehyde having one or more alkyl and/or alkenyl groups on the cyclohexyl ring of cyclohexanal.

For the purposes of the present invention, the term "cyclohexene-1-carbaldehyde compound" refers to cyclohexene-1-carbaldehyde and any derivative of cyclohexene-1-carbaldehyde having one or more alkyl and/or alkenyl groups on the cyclohexenyl ring of cyclohexene-1-carbaldehyde 1.

For the purposes of the present invention, the term "1-cyclohexenyl ketone" refers to any compound having the general formula:

(1)

wherein R1 is alkyl or alkenyl and to any compound including one or more alkyl and/or alkenyl groups on the 1-cyclohexenyl ring of formula 1. An example of a 1-cyclohexenyl ketone is 1-(-1-cyclohexen-1-yl)-ethanone.

For the purposes of the present invention, the term "cyclohexyl ketone" refers to any compound having the general formula:

(2)

wherein R1 is alkyl or alkenyl and to any compound including one or more alkyl and/or alkenyl groups on the cyclohexyl ring of formula 1. An example of a cyclohexyl ketone is cyclohexyl methyl ketone.

For the purposes of the present invention, the term "cyclopentanone" refers to cyclopentanone and any derivative of cyclopentanone including having one or more alkyl and/or alkenyl groups on the ring of cyclopentanone.

For the purposes of the present invention, the term "cyclopentenone" refers to any cyclopentenone, including any cyclopentenone having one or more alkyl and/or alkenyl groups on the ring of cyclopentenone. Examples of cyclopentenones include: 2-cylopenten-1-one and 3-cyclopenten-1-one.

For the purposes of the present invention, the term "cyclopentyl ketone" refers to any compound having the general formula:

(3)

wherein R3 is alkyl or alkenyl and to any compound including one or more alkyl and/or alkenyl groups on the cyclopentyl ring of formula 2. An example of a cyclopentyl ketone is 1-cyclopentyl-ethanone.

For the purposes of the present invention, the term "1-cyclopentenyl ketone" refers to any compound having the general formula:

(4)

wherein R4 is alkyl or alkenyl and to any compound including one or more alkyl and/or alkenyl groups on the 1-cyclopentenyl ring of formula 4. An example of a 1-cyclopentenyl ketone is 1-acetylcyclopentene.

For the purposes of the present invention, the term "1-cyclopentene-1-carboxyaldehyde compound" refers to 1-cyclopentene-1-carboxyaldehyde and any derivative of 1-cyclopentene-1-carboxyaldehyde having one or more alkyl and/or alkenyl groups on the cyclopentenyl ring of 1-cyclopentene-1-carboxyaldehyde.

For the purposes of the present invention, the term "cyclopentaldehyde compound" refers to cyclopentaldehyde and any derivative of cyclopentaldehyde having one or more alkyl and/or alkenyl groups on the cyclopentyl ring of cyclopentaldehyde.

For the purposes of the present invention, the term "detecting device" refers to any type of detecting device capable of detecting the presence of the odorants of the present invention at the concentrations at which the odorants are present in the hydrogen compositions of the present invention or are present in leaks from containers containing the hydrogen compositions of the present invention.

For the purposes of the present invention, the term "flammability limits" refers to a discrete range of fuel/air mixtures whereby a flame will propagate only within this defined range. The term "lower flammability limit" refers to the leanest fuel/air mixture that will allow steady flame propagation. The term "upper flammability limit" refers to the richest fuel/air mixture that will allow steady flame propagation.

For the purposes of the present invention, the term "fluid" refers to any gas or liquid.

For the purposes of the present invention, the term "fuel cell" refers to a device that converts chemical energy directly into electrical energy. The term "fuel cell" is also used broadly to mean any electrochemical cell in which the energy of a reaction between a fuel and an oxidant is converted directly into electrical energy.

For the purposes of the present invention, the terms "furanone" refers to compounds containing a monounsaturated five-membered ring including one oxygen and a carbonyl group, wherein the carbonyl group is part of a ketone functional group or an ester functional group. Examples of furanones include: 2(5H)-furanone, 2(3H)-furanone, 3(2H)-furanone, etc.

For the purposes of the present invention, the term "hydrogen concentration front" refers to the leading edge of a hydrogen cloud as it diffuses through another fluid.

For the purposes of the present invention, the term "hydrogen reflection" refers to the reflection of hydrogen gas off of a barrier.

For the purposes of the present invention, the term "leak zone" refers to the path created by the flow of hydrogen leak through a hole.

For the purposes of the present invention, the term "monounsaturated pyrone" or "monosaturated pyranone" refers to compounds containing a monounsaturated six-membered ring including one oxygen and a carbonyl group, wherein the carbonyl group is part of a ketone functional group or an ester functional group. Examples of monosaturated pyranones include: 5,6-dihydro-2H-pyrane-2-one, 2,3-dihydropyran-4-one, 6H-pyran-3-one, dihyro-2H-pyran-3(4H)-one, etc.

For the purposes of the present invention, the term "not harmful to humans" refers to an exposure to an odorant which is within permissible exposure limits, or within threshold limit values, or within workplace environmental exposure guidelines as set by regulatory agencies such as OSHA, NIOSH, and AIHA respectively.

For the purposes of the present invention, the term "observation point" refers to points within a model selected to compare and study the diffusion of hydrogen through a room or other confined space.

For the purposes of the present invention, the term "odorant" refers to a chemical compound with a smell detectable by a human when the compound is released to the atmosphere. An "odorant" may also indicate a substance that may be readily detectable by a sensor. Preferably, the odorant is detectable below the lower flammability limit of any fuel to which the odorant is added.

For the purposes of the present invention, the term "odorant concentration front" refers to the leading edge of an odorant cloud as it diffuses through another fluid.

For the purposes of the present invention, the term "odorant loading" refers to the concentration of odorant added to hydrogen gas.

For the purposes of the present invention, the term "oxygenate" refers to any chemical compound containing oxygen as part of the chemical structure of the compound. The oxygenate odorants of the present invention are made up solely of carbon, hydrogen and oxygen. However, in some embodiments, the oxygenate odorants of the present invention may be mixed with other odorants and even other oxygenate compounds that include other elements.

For the purposes of the present invention, the terms "pyrone derivative" or "pyranone derivative" refers to monounsaturated and saturated pyrones.

For the purposes of the present invention, the terms "pyrone" or "pyranone" refers to compounds containing a di-unsaturated six-membered ring including one oxygen and a carbonyl group, wherein the carbonyl group is part of a ketone functional group or an ester functional group. Examples of pyranones include: 2-pyrone, 4-pyrone, etc.

For the purposes of the present invention, the term "saturated pyrone" or "saturated pyranone" refers to compounds containing a saturated six-membered ring including one oxygen and a carbonyl group, wherein the carbonyl group is part of a ketone functional group or an ester functional group. Examples of saturated pyranones include: tetrahydro-pyran-3-one, tetrahydro-pyran-4-one.

For the purpose of the present invention the term "smell detectable at less than 1 ppm by a human nose" refers to the minimum required odor detection threshold of a particular odorant to be useful as a hydrogen odorant. The combination of sufficiently low odor threshold combined with sufficiently high vapor pressure allows the odor compound to be in vapor phase at detectable concentration to the conditions under which hydrogen is stored. Odor thresholds cannot yet be accurately predicted, and are generally measured through extensive testing with human subjects in a laboratory setting. Compilations of laboratory data exist in the literature: one example being "Standardized Human Olfactory Thresholds" edited by M. Devos, F. Patte, J. Rouault, P. Laffort, and L. J. Van Gernert, Oxford University Press (1990), the entire contents of which is hereby incorporated by reference.

Description

The oxygenated odorants of the present invention potentially offer a low-cost detection solution A significant challenge for the odorization of hydrogen is compatibility with storage and utilization systems. In particular, an odorant for hydrogen should not poison the catalysts used in hydrogen-fueled fuel cells (e.g., PEMFCs) and should remain in the vapor phase and not decompose under high pressure storage.

In general, odorants are added to gaseous fuels such as natural gas and liquefied natural gas (LNG) in order to provide a means to detect or identify any leakage of such gases. The detection of a leaking gas becomes quite important such that immediate actions or measures may be taken to prevent any harm to life or infrastructure. If gas leaks are not identified, hazards could develop by displacing oxygen where humans may occupy, or accumulate to flammable or explosive concentrations in air.

At fueling stations today, hydrogen dispensers are capable of transferring hydrogen to fuel cell vehicles at pressures greater than 5,000 psi at ambient temperature. Hydrogen storage and dispensing infrastructure is a key safety concern due to the dangers of a high-pressure hydrogen leak combined with hydrogen's wide flammability limits. Having odorized hydrogen available at fueling stations and all along the entire fuel delivery system (from the point of hydrogen production to the point of use) will increase the safety of handling hydrogen. In terms of on-board vehicle storage, a majority of fuel cell vehicles in operation today utilize compressed gas storage tanks. Enhancing the safety of compressed hydrogen cylinders is also a critical need. Odorized hydrogen would enhance the safety of compressed hydrogen cylinders, given a slow or pinhole leak scenario. Other technologies that store hydrogen on-board in solid-state are under investigation (metal hydrides, carbon nanotubes, and glass microspheres) and are inherently safer than compressed or liquid storage of hydrogen. However, with any type of on-board storage device the issue remains with maintaining safety. Accordingly, in at least some embodiments the present invention provides odorants for gaseous fuel compositions that are more stable at high storage pressures, and in particular pressures greater than 5,000 psi. The present invention also provides odorants for gaseous fuel compositions that are more stable at elevated temperature experienced during the filling, delivery or storage of fuel compositions at pressures greater than 5,000 psi.

The odorants of the present invention are also preferably non-toxic to both human beings and the environment at the concentration they are used. The present invention provides odorants for fuel compositions that do not cause harm to the environment, do not impact fuel gas storage, distribution, and delivery infrastructure, does not poison known catalyst materials found in gas leak sensor technologies, post combustion controls, catalytic auto ignition fuel gas reactors, fuel cells, any catalyst materials that function to initiate or accelerate the rate of a chemical or electrochemical reaction involving a fuel gas such as hydrogen, natural gas, propane, LPG, propane or any known gas used as a fuel, accelerant, cooling agent, or process gas. In particular, the present invention provides methods of odorization of hydrogen that is compatible with hydrogen fuel supply systems without interfering with the components and energy conversion efficiency of the system.

Hydrogen, like natural gas, faces similar industrial problems in its application, such as storage, transmission and distribution. In order to protect public welfare and safety, hydrogen needs to be odorized before its large-scale application/utilization by the general public. Natural gas has a set of mature and effective odorization systems for its application, governed by specific federal regulations; however, there are currently no special regulations governing the odorization of hydrogen. Current regulations regarding the safe use, transportation and storage of natural gas are necessary to understand constraints and limitations in choosing a suitable odorant for the hydrogen economy. The codes and standards developed to date have been implemented due to special safety concerns related to the storage, transmission and distribution of natural gas. Mixtures of hydrogen and odorant, therefore, should also comply with current regulations for natural gas odorants. International standards drafted by the International Standards Organization for Hydrogen Technologies (ISO/TC 197) with respect to gaseous hydrogen applications in the transportation sector will provide regulations for storage tanks, filling stations, vehicles and pump connectors, as well as hydrogen product specifications. These draft regulations help gain an understanding of compatibility issues that may arise as a result of adding an odorant. The Department of Transportation (DOT and Occupational Safety and Health Administration (OSHA) have jurisdiction over domestic hydrogen regulations.

To odorize flammable gas, compatible odorants must be carefully selected. Compounds meeting specific criteria may be chosen with consideration for economic factors such as technical feasibility and production cost. An odorant favorable for this purpose should have low solubility in water, good oxidative stability, a minimum defined odor threshold, a minimum defined vapor pressure, and a minimum defined diffusivity. Additionally toxicity, combustibility and other properties of combustion products should be considered. If a single component cannot satisfy all the requirements, blends of two or more components may be used.

Physical and chemical properties of hydrogen that are important to the development of a proper hydrogen odorant include:

| | |
|---|---|
| Lower Flammability Limit (% by volume/air): | 4.0 |
| Lower Detonation Limit (% by volume/air): | 18.3 |
| Stoichiometric Mixture (% by volume/air): | 29.6 |
| Upper Flammability Limit (% by volume/air): | 75.0 |
| Upper Detonation Limit (% by volume/air): | 59.0 |
| Minimum Ignition Energy (mJ): | 0.017 |
| Auto-Ignition Temperature (° C.): | 520° |
| Density @ Standard T/P (Kg/m$^3$): | 0.0827 |
| Viscosity @ Standard T/P ($10^{-6}$ Pa * s): | 8.814 |
| Diffusion Coefficient in Air (cm$^2$/s): | 0.76 |

Hydrogen has a very low density enabling it to readily disperse and mix with air to create explosion or ignition hazards. A hydrogen molecule is very small and has a high diffusion coefficient both in other gases and in solids. When considering hydrogen leaks, its high buoyancy generally affects gas motion considerably more than its high diffusivity. However, the diffusive and dispersive characteristics limit any explosion or ignition hazards in a well-ventilated area. The low viscosity of hydrogen, and its respective flow rate, enhances the hazard of leaks through porous materials, fittings, and seals (i.e. hydrogen has a flow rate approximately 25% higher than methane through the same leak with the same associated pressure drop). Density, diffusivity, and viscosity characteristics should be taken into consideration to select materials used for hydrogen storage devices and to consider compatibility with a suitable odorant.

Characteristically, a higher diffusivity coefficient describes a compound with a lower molecular weight. A compound's diffusivity is dependent upon molecular weight and temperature, rather than the concentration. However, the rate of molecular diffusive transport of a compound is determined from its diffusion coefficient and the concentration gradient of the gaseous compound in an environment and thereby the process of molecular diffusion. As the concentration of a compound within an environment increases so does the frequency of molecular collision thus increasing the rate of mixing. If a given point is the source of gaseous release, then higher concentration lies around that point during a leak event than at any distance x away from that point. Therefore, so long as the distance, x, increases, the concentration of molecules decreases and the magnitude if molecular diffusion (diffusive mixing) decreases. Brownian motion describes the behavior wherein the concentration gradient between any distance, x, and reference point decreases, resulting in slower mixing (lower collision frequency). Hydrogen has its own diffusion coefficient (0.76 cm$^2$/s) by which the magnitude of mixing decreases with distance at a constant rate governed by the change in concentration. Therefore, a longer time is necessary to reach a flammable concentration of H$_2$ at 4% as distance, x, increases away from the source.

The minimum ignition energy of hydrogen is very low. Since most ignition sources generate more than 10mJ of energy, most fuels would ignite if the fuel/air ratio reaches the lower flammability limit. Therefore, the minimum ignition energy, the lower flammability, and detonation limits are important characteristics when selecting a suitable odorant.

Another important property of an odorant is its odor threshold. A suitable odorant should be detectable by the human nose at very low concentrations. In fact, the odor should be detected as soon as hydrogen begins to leak. In order for a compound to be considered as a suitable odorant, it should have a low odor threshold in the gas phase. This factor is important because the odorant will be present as a gas along with hydrogen in the event of a leak. A critical issue in hydrogen odorization is phase compatibility between hydrogen and the odorant at high pressure. To ensure simultaneous outflow in case of a leak, both components should be in the same phase and well blended. Some odor threshold values may be found in *Standardized Human Olfactory Thresholds* edited by M. Devos, F. Pane, J. Rouault, P. Laffort, and L. J. Van Gemert, Oxford University Press (1990). In addition, the American Industrial Hygiene Association (AIHA) publishes a book of odor threshold values (Odor Thresholds for Chemicals with Established Occupational Health Standards).

Physical properties, chemical properties, health hazard information, and odor threshold may be considered when developing the criterion basis for selecting hydrogen odorants. Olfactory power provides an additional basis on which to narrow the possibilities of potential odorants. Based on saturated odorant vapor phase concentration at high pressure, there is a minimum olfactory power required of a successful odorant. Olfactory power first determines odorant loading in the fuel, and odorant loading is further affected by phase equilibrium during fuel storage at high pressure. In regard to phase equilibrium, the odorant may remain in the vapor phase at 6000 psi only at equilibrium limited vapor saturation. Phase calculations therefore show the maximum vapor phase odorant concentration at high pressure. If a low potency odorant is used, like ethanol for example, it is necessary for it to be added to the fuel at very high loadings in order to be detectable. A low potency odorant loaded at high concentration may not satisfy the phase equilibrium requirements of the system. Thus, odorant loading is determined by both olfactory power and phase equilibrium, which may ultimately exclude a potential odorant as a possibility.

Standard olfactory power refers to the minimum concentration at which a particular compound is detectable by the average person. The mathematical definition is given as the negative log of odorant concentration expressed in volumetric fraction: pOl=−log [odorant]. Based on this definition an olfactory power of "0/6/9" corresponds to "odorlessness/1 ppm/1 ppb" threshold levels, respectively. In air, a compound with a greater olfactory power may be detected at lower concentration levels.

One challenge for the odorization of hydrogen is the compatibility of hydrogen and an odorant. At low concentrations an odorant must remain in the vapor phase at detectable concentrations under high-pressure hydrogen storage conditions. To quantitatively validate the concentration of an odorant in the gas phase at high pressure, first order phase equilibrium equations may be used.

When setting up the system, it is assumed that only two components exist, hydrogen ($H_2$) and an odorant (A). It is also assumed that the odorant is saturated. This means that at the constant pressure when odorant is added, the amount of odorant in the vapor phase remains constant. The equation used to find the fraction of the vapor phase taken solely by the odorant is Raoult's Law:

$$x_A P_A^{sat} = y_A P$$

Where, $x_A$ is the odorant's fraction of the liquid phase, $y_A$ the odorant's fraction of the vapor phase, $P_A^{sat}$ is the vapor pressure of the saturated odorant, and P is the total pressure within the system. It takes extreme pressures on the order of 150,000 psi to condense hydrogen at room temperature. From this knowledge it is assumed that no hydrogen will exist in the liquid phase, therefore $x_A$ will equal one:

$$x_A = 1$$

And the equation for becomes:

$$y_A = \frac{P_A^{sat}}{P}$$

With these values, the concentration of odorant may be found at ambient conditions for the storage conditions of greater than 5,000 psi. To calculate the pressure needed to produce a certain saturated concentration of odorant in the vapor phase:

$$P = \frac{P_A^{sat}}{y_A}$$

Where, $$y_A = \frac{[odorant(ppm)]}{1 \times 10^6}$$

Another challenge for the odorization of hydrogen is compatibility with storage and utilization systems. In particular, an odorant for hydrogen should not poison the catalysts used in hydrogen-fueled fuel cells (e.g., PEMFCs) and should remain in the vapor phase and not decompose under high pressure storage. Natural gas is typically odorized with mercaptans and sulfides. These sulfur compounds provide high olfactory response and, in blends, may meet most natural gas storage/safety criteria. However, it is known that sulfur compounds will adversely affect fuel cell performance.

Another class of odorants is nitrogen containing compounds such as ammonia ($NH_3$) and amines ($R3_{-x}NH_x$). It has been reported that trace ammonia decreases the performance of a PEMFC, with the extent of degradation dependant on the concentration and the exposure time to this compound, see Halseid et al. "Effect of ammonia on the performance of polymer electrolyte membrane fuel cells," *J. Power Sources*, 154, 343-350 (2006) (Halseid et al. 2006) and Soto et at., "Effect of transient ammonia concentrations on PEMFC performance," *Electrochem. Solid-State Lett.*, 6 (7) A 133-A 135 (2003). For example, significant degradation occurred within 3 hours on exposure to 10 ppm $NH_3$ in hydrogen. Some reversibility in fuel cell performance was observed, however, full recovery was not achievable even if the catalyst was exposed to with much lower concentration of $NH_3$ in hydrogen (1 ppm), see Halseid, et al. and Halseid et al., "Oxidation of ammonium on platinum in acidic solutions," *J. Electrochem. Soc.*, 154 (2) B263-B270 (2007) (Halseid et al. 2007). Ammonia in the anode stream is found to hinder the rate of hydrogen oxidation and oxygen reduction in the catalyst layer by forming stable nitrogen or nitrogen-oxygen species on the platinum surface due to the electrochemical activity of the ammonia, see Halseid, et al. 2006 and 2007. Furthermore, the ammonium ions derived from ammonia may replace the protons in the ionomer of the catalyst layer as well as in the electrolyte membrane, which results in higher resistance in the membrane-electrode assemblies (MEAs), see Halseid et al 2006; Uribe, et al., "Effect of ammonia as potential fuel impurity on proton exchange membrane fuel cell performance," *J. Electrochem. Soc.*, 149 (3) A293-A296 (2002) and Rockward et al., "The effects of multiple contaminants on polymer electrolyte fuel cells," *ECS Transactions*, II (1) 821-829 (2007). For these reasons, sulfur and/or nitrogen free compounds may overcome such fuel cell compatibility issues.

For compatibility with hydrogen and the hydrogen fueled fuel cell infrastructure, the hydrogen odorant should therefore be a non-sulfur based odorant. Also, many current odorants do not meet diffusivity and vapor pressure requirements for the odorant to be effective in hydrogen systems. Good diffusivity is important to ensure that the odorant will diffuse with hydrogen that is leaking from a container, such as a fuel cell, combustor or pipe. It is also desirable that the odor be detectable at relatively low concentration and be in vapor phase even at a high pressure.

U.S. Pat. No. 7,182,796 to Kato (Kato), entitled "Odorant for Fuel Gas," issued Feb. 27, 2007, describes odorants for fuel gas including hydrogen that have a detection threshold of <1 ppb, containing no sulfur and no nitrogen. But these odorants have several drawbacks. For example, the odorants described in Kato do not meet the required characteristics of the odorants described in U.S. Patent Application No. 2004/0031314 entitled "Hydrogen Odorization System and Method," published Feb. 19, 2004, the entire contents and disclosure of which is hereby incorporated by reference. For example, the odorants described in Kato does not exert a a vapor pressure of at least 0.5 psi, that would allow these odorants to be in the vapor phase at detectable concentrations at hydrogen storage pressures up to 5,000 psi and above. In addition the odorants described in Kato are generally solids at ambient temperature, making addition of the odorants to a fuel gas problematic for commercial applications. Furthermore, although odorants described in Kato are the to impart an unpleasant odor to fuel gas, several of the odors described in Kato may be considered pleasant smelling, contrary to the objective of imparting an alarming odor to leaking fuel. For example, the following odorants described in Kato have what would generally be considered pleasant odors: ethyl vanillin (vanilla like odor), furaneol (strawberry/fresh pineapple type odor), 2-methoxy naphthalene (orange flower/acacia like odor), and γ-nonalactone (coconut odor).

U.S. Pat. No. 6,820,464 to Puri et al. (Puri '464), entitled "Odorized Seals for the Detection of Gas Leak", issued Nov. 23, 2004 and U.S. Pat. No. 7,229,831 to Puri (Puri '831), entitled "Leak Site Odorization for Gas leak Detection", issued Jun. 12, 2007, describe the use of C4-C7 acrylic acid alkyl esters (methyl acrylate, ethyl acrylate, propyl acrylate, butyl acrylate), carboxylic acids and combinations thereof as hydrogen odorants. The odorant compositions described in Puri '464 and '831 are acyclic and may not possess sufficient chemical stability in the presence of high pressure hydrogen, particularly at refueling conditions where temperatures may range from −40 to 85° C.

U.S. Pat. No. 7,267,901 to Miura et al (Miura et al.), entitled "Fuel cell system", issued Sep. 11, 2007, describes use of butyric acid, another acyclic compound, as an odorant for hydrogen applications. However, such acyclic structures may not possess sufficient chemical stability in the presence of high pressure hydrogen, particularly at refueling conditions where temperatures may range from −40 to 85° C.

International Patent Nos. WO 2006/067111, WO 2006/067113, and WO 2006/067115 describe using one or more acrylic acid C1-C6-alkyl esters in combination with other odorant compositions (methyl salicylate, indene and one or more C5-alky esters (n-amyl amyl acetate or isoamyl acetate), respectively. The C1-C6-alkyl esters are acyclic, like the compounds described in Puri et at., and may not possess sufficient chemical stability in the presence of high pressure hydrogen, particularly at refueling conditions where temperatures may range from −40 to 85° C. Methyl salicylate is also undesirable as an odorant for commercial application due to its toxicity in pure form.

With the current policies of the Federal, State, and international governments, it becomes important for odorants to be developed that do not cause harm to the environment, increase or enhance concerns for global climate change, pose a health or welfare concern to the public, or pose toxicity concerns to humans or biological species within the environment. It is noted that that during the combustion of a fuel composition that includes odorant for leak detection, it therefore is desirable for odorants that do not include nitrogen or sulfur species such that nitrogen oxides ($NO_x$) or sulfur oxides, such as $SO_2$, are formed as combustion products.

The odorants of the present invention comprises are compounds that have no nitrogen atoms in their molecules and thereby do not pose concern for the generation of nitrogen oxide emissions when employed in combustion applications. Likewise, the odorants of the present invention comprise compounds that have no sulfur atoms in their molecules and thereby do not generate sulfur oxide emissions. As a result, such odorants of the present invention do not cause sulfur poisoning of catalysts used for fuel cells, and do not pose additional nitrogen or sulfur loading to the environment.

In one embodiment, the present invention provides odorized hydrogen gas compositions for use in high pressure hydrogen storage and in hydrogen-fueled fuel cells that remain stable and do not decompose under high pressure storage and are not deleterious to the fuel cell infrastructure or the environment.

Classes of compounds that merit consideration as hydrogen odorants are organic oxygenate odorants. Specific compounds derived from the ketone, aldehyde, ester, and carboxylic acid functionalities indicate moderate olfactory response, and are generally compatible with hydrogen fuel cell catalysts.

Many possible odorous organic hydrocarbons containing oxygen exist, characterized by the general formula, $C_nH_{2n\pm x}O_z$, where n, x and z are integers. But only some of these oxygen-containing compounds may be advantageously used as hydrogen odorants.

The oxygenate odorants of the present invention are made from carbon, hydrogen and oxygen only. The oxygenate odorants of the present invention are non-sulfur based odorants. The odorants have appropriate physical and chemical properties considered to be compatible with hydrogen, and hydrogen powered infrastructure. These compounds possess a unique and distinctive odor unlike odorants used for natural gas, and provide ample human sensory detection prior to dangerous hydrogen accumulation.

The oxygenate odorants of the present invention meet all of the following criteria: (1) the odorant is relatively benign to fuel cell catalyst materials; (2) if the odorant reacts with the fuel cell materials, the odorant will form water and hydrocarbons if fully reduced under a hydrogen atmosphere; (3) if the odorant reacts with the fuel cell materials the fuel cell exhaust gas produced will be relatively odorless; (4) the odorant is relatively stable under typical storage conditions for hydrogen gas; (5) the odorant is environmentally benign; (6) the odorant has a vapor pressure of about 0.002 psi or greater at 25° C. at 1 atm and (7) the odorant has a smell detectable at less than 1 ppm by a human nose. In some embodiments, the oxygenate odorants of the present invention may have a vapor pressure in the range from about 0.002 psi to about 12 psi at 25° C. and 1 atm. In some embodiments, the oxygenate odorants of the present invention may have a vapor pressure greater than 0.5 psi at 25° C. and 1 atm.

Figure 1:
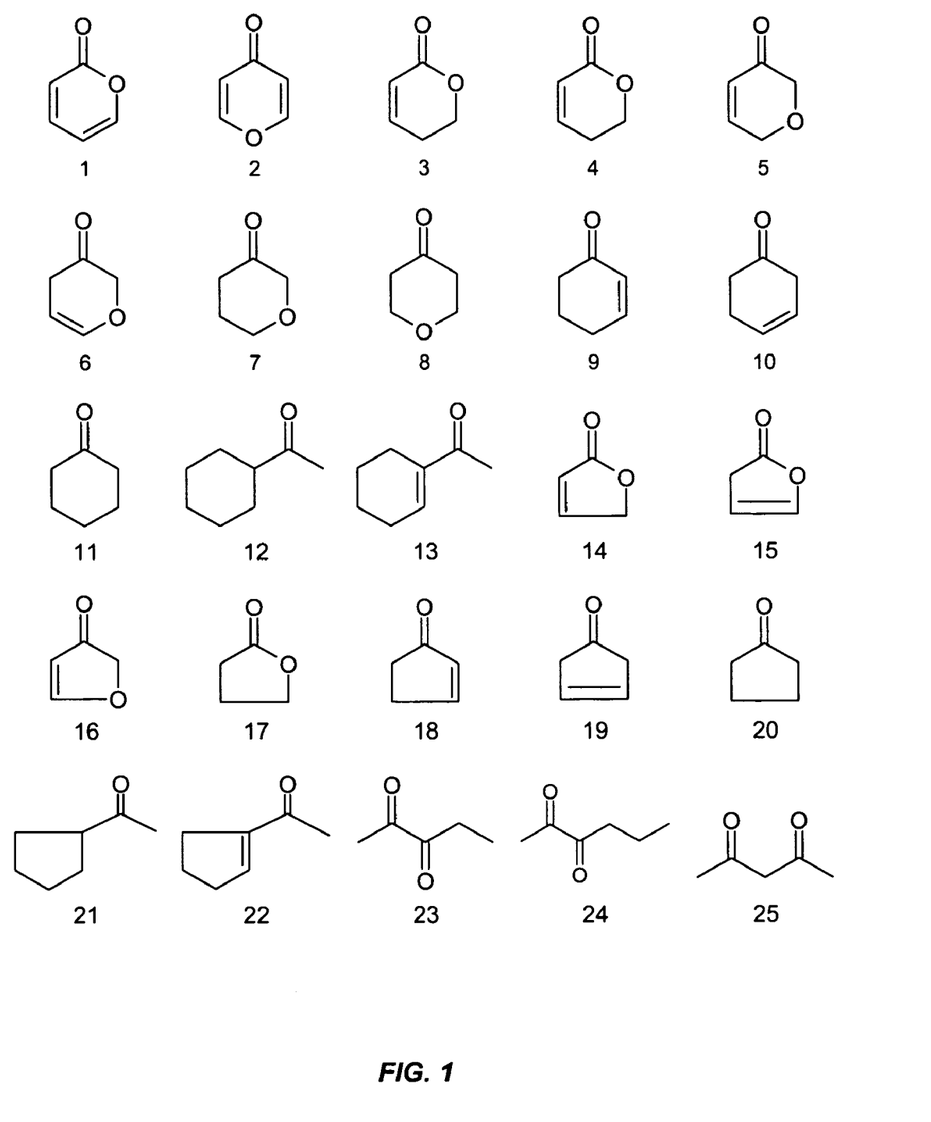
FIG. 1 illustrates the cherkical structures of oxygenate odorants according to the present invention.
Figure 2:
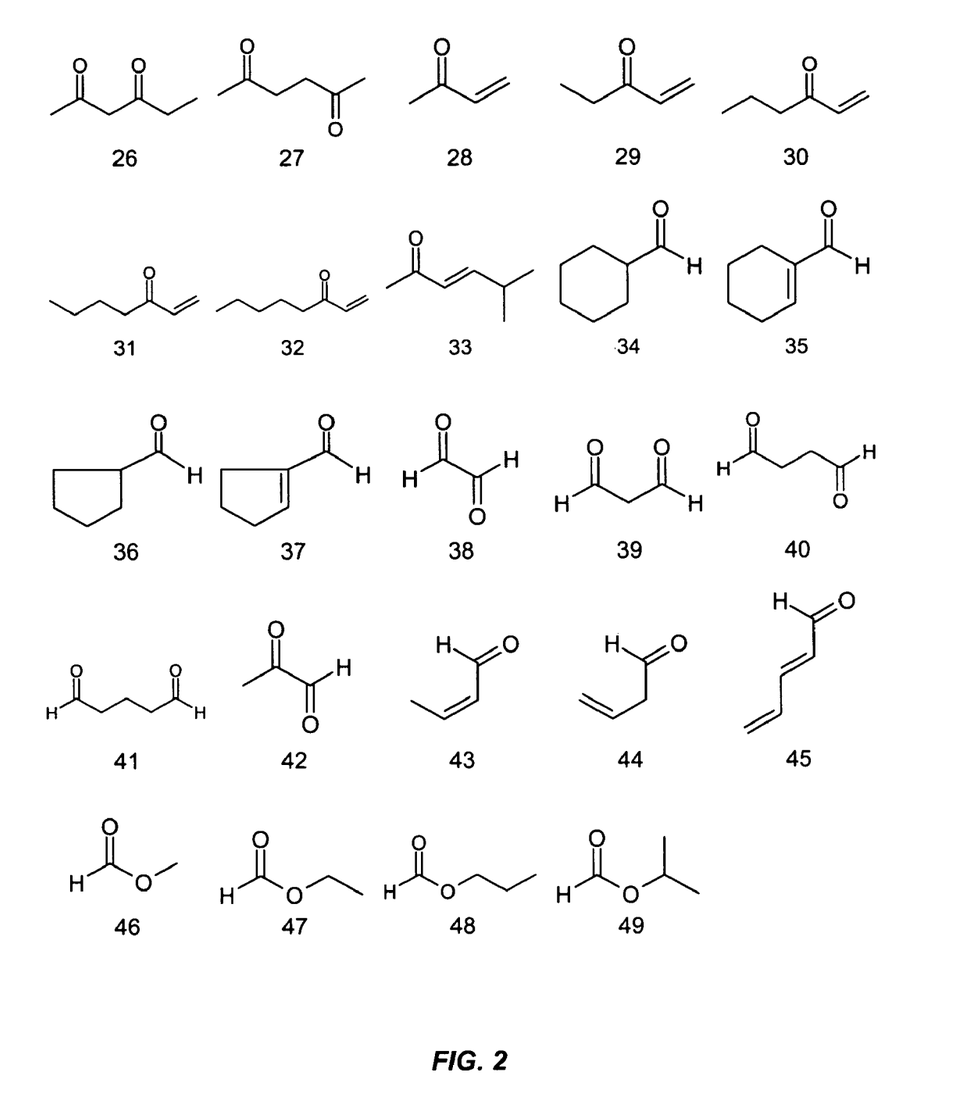
FIG. 2 illustrates the chemical structures of oxygenate odorants according to the present invention.

Examples of oxygenate odorants that meet criteria or should meet the criteria of 1-7 above are compounds 1-49 listed in Tables 1 and 2 below. The chemical structures of compounds 1-25 and 26-49 are shown in FIGS. 1 and 2, respectively. The compositions listed in Tables 1 and 2 are not exclusive, but rather intended to be a representative listing of odorants. Isomers, and/or alkyl (C1-C7 mono-substituted, di-substituted or multi-substituted), and/or alkenyl (C1-C7 mono-substituted, di-substituted or multi-substituted) derivatives of the compounds listed in Tables 1 and 2 and shown in FIGS. 1 and 2 may also be used as oxygenated odorants in the hydrogen gas compositions of the present invention. In Tables 1 and 2, for compounds for which vapor pressure data at 25° C. and 1 atm is not provided, it is believed that these compounds have a vapor pressure of at least 0.002 psi at 25° C. and 1 atm based on the molecular weight of these compounds and the similarity in structure and chemical functionality of these compounds to other compounds in Tables 1 and 2.

TABLE 1

| # | Name | CAS | nC | nH | nO | MW (g/mol) | BP (° C.) | MP (° C.) | Pvap @ 20° C. (psi) | Pvap @ 25° C. (psi) |
|---|------|-----|----|----|----|------------|-----------|-----------|---------------------|---------------------|
| 1 | 2-Pyrone | 504-31-4 | 5 | 4 | 2 | 96.1 | 208 | 9 | | 0.005 |
| 2 | 4-Pyrone | 108-97-4 | 5 | 4 | 2 | 96.1 | 215 | 33 | | 0.004 |
| 3 | 5,6-Dihydro-2H-pyran-2-one | 3393-45-1 | 5 | 6 | 2 | 98.1 | | | | |
| 4 | 2,3-Dihydropyran-4-one | | 5 | 6 | 2 | 98.1 | | | | |
| 5 | 6H-pyran-3-one | | 5 | 6 | 2 | 98.1 | | | | |
| 6 | Dihydro-2H-pyran-3(4H)-one | 23462-75-1 | 5 | 5 | 2 | 98.1 | | | | |
| 7 | Tetrahydro-pyran-3-one | | 5 | 8 | 2 | 100.1 | | | | |
| 8 | Tetrahydro-pyran-4-one | 29943-42-8 | 5 | 8 | 2 | 100.1 | | | | |
| 9 | 2-Cyclohex-2-en-1-one | 930-68-7 | 6 | 8 | 1 | 96.1 | 172 | −53 | | 0.07 |
| 10 | 3-Cyclohex-1-one | 4096-34-8 | 6 | 8 | 1 | 96.1 | | | | 0.04 |
| 11 | Cyclohexanone | 108-94-1 | 6 | 10 | 1 | 98.2 | 156 | −16 | | 0.08 |
| 12 | Cyclohexyl methyl ketone | 823-76-7 | 8 | 14 | 1 | 126.2 | 182 | | | .02 |
| 13 | 1-(1-Cyclohexen-1-yl)-ethanone | 932-66-1 | 8 | 12 | 1 | 124.2 | 204 | 75 | | 0.003 |
| 14 | 2(5H)-Furanone | 497-23-4 | 4 | 4 | 2 | 84.1 | 5 | | | 0.02 |
| 15 | 2(3H)-Furanone | 20825-71-2 | 4 | 4 | 2 | 84.1 | | | | 0.02 |
| 16 | 3(2H)-Furanone | | 4 | 4 | 2 | 84.1 | | | | |
| 17 | γ-Butyrolactone | 96-48-0 | 4 | 6 | 2 | 86.1 | 205 | −45 | 0.03 | 0.01 |
| 18 | 2-Cyclopenten-1-one | 930-30-3 | 5 | 6 | 1 | 82.1 | 138 | | | 0.18 |
| 19 | 3-Cyclopenten-1-one | 14320-37-7 | 5 | 6 | 1 | 82.1 | | | | |
| 20 | Cyclopentanone | 120.92-3 | 5 | 8 | 1 | 84.1 | 131 | −51 | | 0.22 |
| 21 | 1-Cyclopentyl-ethanone | 6004-60-0 | 7 | 12 | 1 | 112.2 | | | | 0.07 |
| 22 | 1-Acetylcyclopentene | 16112-10-0 | 7 | 10 | 1 | 110.2 | | | | |
| 23 | 2,3-Petanedione | 600-14-6 | 5 | 8 | 2 | 100.1 | 111 | −52 | | 0.60 |
| 24 | 2,3-Hexanedione | 3848-24-6 | 6 | 10 | 2 | 114.2 | 130 | | 0.19 | 0.06 |
| 25 | Aceylacetone | 123-54-6 | 5 | 8 | 2 | 100.1 | 140 | −23 | 0.13 | 0.06 |

TABLE 2

| # | Name | CAS | nC | nH | nO | MW (g/mol) | BP (° C.) | MP (° C.) | Pvap @ 20° C. (psi) | Pvap @ 25° C. (psi) |
|---|------|-----|----|----|----|------------|-----------|-----------|---------------------|---------------------|
| 26 | 2,4-Hexandione | 3002-24-2 | 6 | 10 | 2 | 114.2 | 160 | | | 0.06 |
| 27 | 2,5-Hexanedione | 110-13-4 | 6 | 10 | 2 | 114.2 | 181 | −6 | 0.01 | 0.06 |
| 28 | Methyl vinyl ketone | 78-94-4 | 4 | 6 | 1 | 70.1 | 81 | <25 | | 2.94 |
| 29 | Ethyl vinyl ketone | 1629-58-9 | 5 | 8 | 1 | 84.1 | 103 | | | 0.74 |
| 30 | Propyl vinyl ketone | 1629-60-3 | 5 | 10 | 1 | 86.2 | | | | |
| 31 | Butyl vinyl ketone | | 7 | 12 | 1 | 112.2 | | | | |
| 32 | Pentyl vinyl ketone | 4312-99-6 | 8 | 14 | 1 | 126.2 | | | | |
| 33 | 5-Methyl-3-hexen-2-one | 5166-53-0 | 7 | 12 | 1 | 112.2 | | | | 0.19 |
| 34 | Cyclohexanal | 2043-61-0 | 7 | 12 | 1 | 112.2 | 162 | | | 0.05 |
| 35 | Cyclohexene-1-carbaldehyde | | 7 | 10 | 1 | 110.2 | | | | |
| 36 | Cyclopentaldehyde | 872-53-7 | 6 | 10 | 1 | 98.2 | 141 | | | 0.17 |
| 37 | 1-Cyclopentene-1-carboxaldehyde | 6140-65-4 | 6 | 8 | 1 | 96.1 | | | | |
| 38 | Ethanedial | 107-22-2 | 2 | 2 | 2 | 58.0 | 51 | 15 | | 4.93 |
| 39 | Malondialdehyde | 542-78-9 | 3 | 4 | 2 | 72.1 | | 72 | | 0.09 |
| 40 | Butanedial | 638-37-9 | 4 | 6 | 2 | 86.1 | 171 | | | |
| 41 | Pentane-1,5-dial | 111-30-8 | 5 | 8 | 2 | 100.1 | 103 | −4 | | 0.01 |
| 42 | 2-Oxo-propanal | 78-98-8 | 3 | 4 | 2 | 72.1 | 74 | 25 | | 0.52 |
| 43 | 2-Butenal | 4170-30-3 | 4 | 6 | 1 | 70.1 | 102 | −76 | | 0.58 |
| 44 | 3-Butenal | 7319-38-2 | 4 | 6 | 1 | 70.1 | | | | |

TABLE 2-continued

| # | Name | CAS | nC | nH | nO | MW (g/mol) | BP (° C.) | MP (° C.) | Pvap @ 20° C. (psi) | Pvap @ 25° C. (psi) |
|---|---|---|---|---|---|---|---|---|---|---|
| 45 | Penta-2,4-dienal | | 5 | 6 | 1 | 82.1 | | | | |
| 46 | Methyl formate | 107-31-3 | 2 | 4 | 2 | 60.1 | 32 | −100 | | 11.33 |
| 47 | Ethyl formate | 109-94-4 | 3 | 6 | 2 | 74.1 | 54 | −80 | | 4.74 |
| 48 | Propyl formate | 110-74-7 | 4 | 8 | 2 | 88.1 | 81 | −93 | 1.60 | |
| 49 | Isopropyl formate | 625-55-8 | 4 | 8 | 2 | 88.1 | 68 | −80 | 2.67 | |

In Tables 1 and 2:
CAS = The CAS number assigned to the compound.
nC = number of carbon atoms.
nH = number of hydrogen atoms.
nO = number of oxygen atoms.
MW = Molecular weight (g/mol).
BP = Boiling Point (° C.).
MP = Melting point (° C.).
Pvap @ 20° C. = Vapor pressure in pounds per square inch (psi) at 20° C. and 1 atm.
Pvap @ 25° C. = Vapor pressure in pounds per square inch (psi) 25° C. (psi) and 1 atm.

As may be seen in Tables 1 and 2 and FIGS. 1 and 2, the oxygenate compounds of the present invention may be cyclic or acyclic. The cyclic compounds may include five-membered rings or six-membered rings and may include homocyclic or heterocyclic rings. The homocyclic and heterocyclic rings may be saturated or unsaturated. The cyclic oxygenate compound of the present invention may be: a pyrone/pyranone (such as compounds 1 and 2), a monosaturated pyrone/pyranone (such as compounds 3, 4 5 and 6); a saturated pyrone/pyranone (such as compounds 7 and 8); a cyclohexenone (such as compounds 9 and 10); a cyclochexanone (such as compound 11); a cyclohexyl ketone (such as compound 12); a 1-cyclohexenyl ketone (such as compound 13); a furanone (such as compounds 14, 15 and 16); a butyrolactone (such as compound 17); a cyclopentenone (such as compounds 18 and 19); a cyclopentanone (such as compound 20); a cyclopentyl ketone (such as compound 21); a 1-cyclopentenyl ketone (such as compound 22); a cyclohexanal (such as compound 34); a cyclohexene-1-carbaldehyde compound (such as compound 35); a cylopentaldehyde (such as compound 36); or a 1-cyclopentene-1-carboxaldehyde compound (such as compound 37). The acyclic oxygenate compounds of the present invention may be: a diketone having at least five carbon atoms (such as compounds 23, 24, 25, 26 and 27); an alkyl vinyl ketone such as compounds 28, 29, 30, 31 and 32); a 5-methyld-2-hexon-2-one (such as compound 33); an acyclic dialdehyde (such as compounds 38, 39, 40 and 41); a 2-oxo-propanal (such as compound 42); a acyclic unsaturated aldehyde (such as compounds 43, 44 and 45); or an alkyl formate (such as compounds 46, 47, 48 and 49).

The oxygenated odorants of the present invention may be used while hydrogen gas is being stored, being distributed through pipes, being dispensed as a fuel from a fuel dispensing apparatus, etc. The odorant may also be used in the hydrogen gas in a fuel cell for a device, such as a motor vehicle.

The oxygenate odorants of the present invention are more benign toward the fuel cell catalyst and membrane materials compared to odorants containing other nitrogen, sulfur and selenium. Many sulfur-containing and nitrogen-containing odorants are known to poison the fuel cell catalyst.

If the oxygenate odorants of the present invention are reactive over fuel cell catalyst materials, the oxygenate odorants of the present invention will form water and hydrocarbon if fully reduced under hydrogen atmosphere, unlike odorants containing sulfur and selenium which may form $H_2S$ and $H_2Se$, respectively, upon reduction. Therefore, the possible reaction products of the oxygenates with the fuel cell catalyst, such as the PEM fuel cell catalyst, are odorless and will not impart an additional odor to the fuel cell exhaust gas. The reaction products and extent of reaction (deodorization) depends on the reactivity of the oxygenate. The consumption and reaction of odorant over the fuel cell catalyst also minimizes or negates the need at the fuel cell stack exhaust for an odorant removal device, such as the adsorber system described in U.S. Patent Application No. 2004/0031314.

The stability of the oxygenated odorants of the present is important under storage conditions. While filling a high pressure hydrogen storage tank, compression of hydrogen in the tank results in temperature increase. As a result the oxygenated odorants of the present invention exhibit sufficient thermal stability to withstand the combination of temperature and hydrogen pressure, such that the odorant does not decompose.

Oxygenated odorants that are cyclic compounds, such as pyrones, monounsaturated pyranones, saturated pyranones, cyclohexyl ketones, 1-cyclohexenyl ketones, butrolactones, cyclopentenones, cyclopentanones, cyclopentyl ketones, 1-cyclopentenyl ketones, cyclohexanal compounds, cyclohexene-1-carbaldehyde compounds, cyclopentaldehyde compounds, 1-cyclopentene-1-carboxyaldehyde compounds, etc. provide particularly enhanced stability compared to acyclic compounds. Examples of such cyclic compounds are compounds 1-22 and 34-37 of Tables 1 and 2 and FIGS. 1 and 2. The stability of the oxygenate odorant under conditions of fuel storage is important to the degree that the odorant does not decompose under temperature and pressure conditions experienced during refueling. The cyclic structure of these oxygenated compounds of the present invention may provide the necessary degree of thermal stability in the presence of high pressure hydrogen.

The oxygenated odorants of the present invention are generally more environmentally benign than odorants containing nitrogen, sulfur and selenium.

The oxygenated odorants of the present invention also meet the the criteria set forth for preferred odorants in described in U.S. Patent Application No. 2004/0031314 entitled "Hydrogen Odorization System and Method," published Feb. 19, 2004, the entire contents and disclosure of which is hereby incorporated by reference.

In one embodiment the odorant comprises 0.01 to 1000 ppm of the composition comprising or consisting essentially of hydrogen gas and the odorant.

The odorant preferably has one or more of the following characteristics: (1) a olfactory power of about 7.0 or more, (2)

a diffusivity of about 0.012 cm$^2$/s or more and (3) a molecular weight of about 200 g/mol or less.

The percentage of the composition that is odorant, the minimum olfactory power of the odorant, the minimum diffusivity of the odorant and the maximum molecular weight of the odorant in the embodiments described above are chosen based on the conditions under which hydrogen will generally be stored and utilized. Certain minimum characteristics or physical properties are demanded of the odorant in order for it to function adequately with respect to detectability, phase equilibrium at high pressure, and odorant dispersion in air relative to hydrogen. The oxygenated odorants of the present invention meet these minimum requirements.

Another consideration for the odorant is the stability of the odorant with respect to fueling requirements. While filling a high pressure hydrogen storage tank, compression of hydrogen in the tank results in temperature increase. As a result the odorant must exhibit sufficient thermal stability to withstand the combination of temperature and hydrogen pressure, such that the odorant does not decompose. The odorants suggested herein are mainly cyclic and acyclic hydrocarbons containing oxygen. The cyclic structure enhances the stability of the odorants, relative to other acyclic oxygenates, under high pressure and during temperature cycles as a high pressure hydrogen storage tank is filled.

In some embodiments, two or more different odorants may be used with the gaseous compositions of the present invention. For example, a mixture of two or more of 1-49 may be used to odorize a gaseous composition. Also, the odorants of the present invention may be mixed with another type of odorant compound, such as the selenium, oxygen, nitrogen and sulfur compounds described in U.S. Patent Application No. 2004/0031314 and such mixtures may be used to odorize a gaseous composition.

The fuel cell systems of the present invention may include self-contained fuel supplies or cartridges, stationary fuel cell systems that are often connected to large storage tanks or pipelines that may provide a continuous flow single chamber fuel cell systems, and dual chamber fuel cell systems. However, other fuel cell systems may also employ the odorants and odorant compositions of the present invention, and the selected embodiments being described are only exemplary in nature. Each fuel cell includes an anode, a cathode, and an electrolyte. The electrolyte may include a solid oxide membrane, a polymer membrane, or other membrane used for other fuel cell types. It will be understood, however, that the fuel cell system is not limited to the anode/electrolyte/cathode configuration. Other fuel cell systems, for example porous supports and current collector supported systems may also be used.

Figure 3:
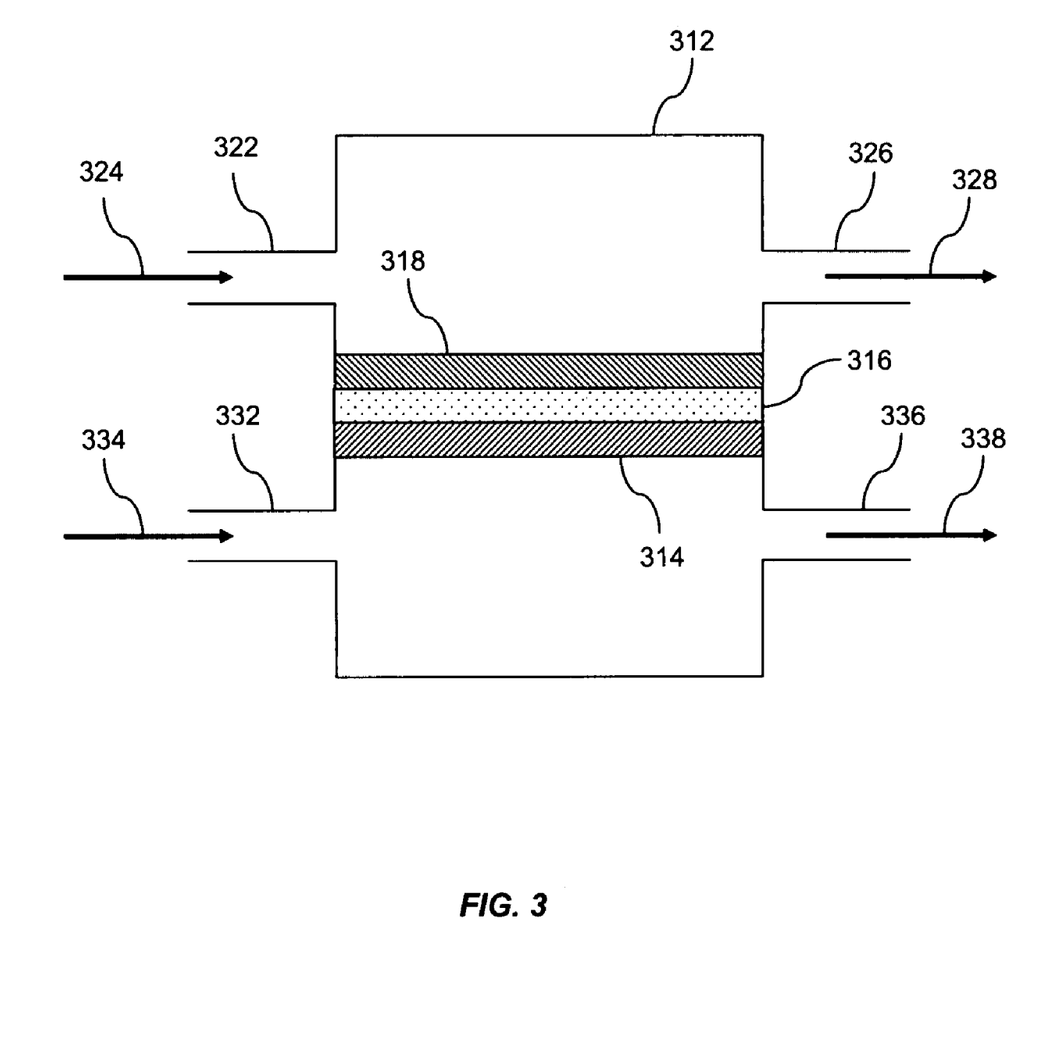
FIG. 3 is a schematic diagram of a fuel cell system in which the oxygenate odorants of the present invention may be used.

FIG. 3 shows an exemplary fuel cell 302 in which the oxygenate odorants of the present invention may be employed. Within a fuel cell housing 312 are an anode 314, an electrolyte 316 and a cathode 318. A supply of oxidant enters fuel cell housing 312 at an entry port 322 as indicated by arrow 324. Oxidant exhaust/offgas exits fuel cell housing 312 at an exit port 326 as indicated by arrow 328. A supply of fuel enters fuel cell housing 312 at an entry port 332 as indicated by arrow 334. Fuel exhaust/offgas exits fuel cell housing 312 at an exit port 336 as indicated by arrow 338.

The self-contained fuel supply may house any of a number of various fuels for introduction to the anode of the fuel cell, such as the fuel cell of FIG. 3. The type of fuel depends on the fuel cell type. For example, if the fuel cell is a solid oxide fuel cell, the fuel may be hydrogen, hydrocarbons, or alcohols. However, if the fuel cell is a direct methanol fuel cell, the fuel may be methanol.

In addition to containing a fuel, the self-contained fuel supply also includes one of the odorants described herein. The odorant is added or injected into the self-contained fuel supply as a leak indicator. In the event of a leak, the odorant provides such notice to humans local to the fuel cell system. Accordingly, the odorant may be added to the self-contained fuel supply before, after, or at the same time the fuel is added. However, instead of a self-contained fuel supply a stationary fuel cell system is in fluid communication with a continuous supply of fuel via a supply line. The supply line provides odorized fuel to the fuel cell. The fuel may be odorized in one or more ways.

The use of organic molecules as odorants detectable by humans, the organic odorants may also be used in combination with a sensor designed to send the presence of specified organic compounds described herein. The sensor may be coupled to the fuel supply, a fuel cell, or some other component of the fuel cell system, a combustor, a combustion system, a vehicle control system, or any vehicle component. The sensor may be located in proximity to the self-contained fuel supply, the fuel cell, or both, enabling the sensor to quickly detect any leaks. The sensor may also include circuitry programmed to shut down the fuel cell system or other systems or components described above in the event of a detected leak. The addition of the sensor may facilitate use of organic odorants at very low concentrations that are not detectable by humans for special applications or circumstances. Furthermore, the organic odorant molecule may be chosen so that extremely high sensitivity and selectivity of the sensor is realized to avoid false alarms.

Fuel cells conduct an electrochemical reaction to produce electrical power. The typical fuel cell reactants are a fuel sources such as hydrogen or a hydrocarbon, and an oxidant such as air, or oxygen. Fuel cells provide a DC (direct current) that may be used to power any electrical device (i.e. Electric drive trains, motors, appliances, lights, etc). There are several types of fuel cells, each using a different chemistry.

Fuel cells typically include three basic elements: an anode, a cathode, and an electrolyte. Usually the anode and cathode are sandwiched around the electrolyte. The electrolyte prohibits the passage of electrons. Fuel cells are usually classified by the type of electrolyte used. The fuel cell types are generally characterized into several groups: proton exchange membrane (PEM) fuel cells, direct methanol fuel cells (DMFC), alkaline fuel cells (AFC), phosphoric-acid fuel cells (PAFC), solid oxide fuel cells (SOFC), molten carbonate fuel cells (MCFC), molten hydride fuel cells (MHFC), and high temperature fuel cells.

The anode and cathode are generally porous (although in the case of an MHFC the cathode may be a dense palladium film) and usually includes an electrocatalyst, however, each may have a different chemistry. Fuel migrates through the porous anode and an oxidant migrates through the porous cathode. The fuel and oxidant react to produce various charged particles, which include electrons at the anode. The electrons cannot pass through the electrolyte and therefore creates an electrical current that may be directed to an external circuit. The cathode conducts the electrons back from the external circuit, where they recombine with various ions and oxygen and may form water and/or other by-products. Often a number of fuel cells are arranged in a stack to provide a desired amount of electrical power.

Fuel for facilitating the fuel cell reaction is generally either self-contained for provided by a supply system (such as a pipeline or storage tank) that may present a continuous flow. Portable fuel cells typically include the self-contained fuel supplies or cartridges that may be refilled or replaced. Other fuel cells, such as large industrial fuel cells, are often connected to larger storage tanks or pipelines that may be provided with a continuous flow at larger volumes. However, with both self-contained and continuous flow fuel supplies, it is currently very difficult to detect leaking fuel supplied to fuel cells. Most of the fuels used for fuel cells are colorless and odorless, and current sensor systems cannot be distributed to the level of density that may provide detection for all leaks events that may occur along the entire fuel storage and delivery system. Therefore, until there are fully redundant leak detection systems in place, and there is a leak detection technology that may provide an independent verification of a leak where sensors are not instrumented or placed with sufficient density due to cost or logistical constraints it is unlikely that all fuel leaks will be noticed. Any undetected fuel leak may lead to hazardous conditions or result in the inefficient operation of the fuel cell.

Some fuel cells, such as SOFCs mentioned, may receive fuel from public supplies, such as natural gas pipelines, public gas supplies are already odorized with sulfur compounds, which provide a strong and recognizable odor. Therefore, fuel cell system leaks may be easily detected when connected to public natural gas supplies. However, sulfur is a known poison of fuel cell anodes and gas reformers (that may be used, with SOFCs), eventually rendering them ineffective. Therefore, sulfur-removal systems have been employed to remove the sulfur from the fuel prior to reaching the fuel cell anodes, however, such methodology provides for added cost, complexity, weight, volume, and reduced fuel pressure. Also, when sulfur-removal systems are used, a sulfur collection system is also required for the sulfur compounds that are removed from the fuel stream. Therefore, it becomes desirable to provide odorants for fuel compositions where the odorant constituents do not pose any poisoning concern, and minimize or eliminate any impacts to the operation or efficiency of the fuel cell.

In one of many possible embodiments, the present invention provides odorants for fuel compositions that facilitate the detection of fuel leaks in the fuel storage and delivery infrastructure supplying, passing through, being consumed by, reduced by, or reacting with a fuel cell or components of a fuel cell. The present invention provide odorants for gaseous fuel compositions that supply fuel cells, that are benign to the environment, that are benign to the components of a fuel cell such as a fuel cell electrode catalyst, the electrolyte in a fuel cell, so that gas detection is achieved during any leak event that would occur across a fuel storage, or fuel delivery system that is intended to supply gas to a fuel cell, pass through, or be consumed or reduced in a fuel cell. The present invention also provide odorants for fuel compositions that remain benign to the environment, to humans and biological species at the exit of a fuel cell, when such odorants pass through a fuel cell and remain constituents of a fuel cell off gas.

In some embodiment, the present invention to provide odorants for fuel compositions that may be easily scrubbed or removed from a fuel delivery system, scrubbed or removed from a fuel delivery system supplying a fuel cell, combustor, or process, and or scrubbed or removed from the exit, offgas, or flue gas from a fuel cell, combustor, or process. The present invention also provides odorants for fuel compositions that may be removed by specially designed or commercially available adsorption or absorption processes, may be removed or scrubbed in a water trap, or humidifier system based on odorant solubility in water. In addition, the present invention provides odorants for gaseous fuel compositions that are benign to the environment, that are benign to the components of a combustion system, that are benign to the environment as combustion products, and that do not pose health or toxicity concerns to humans or biological species.

The present specification provides odorants for detection fuel leaks in a fuel cell system, preferably by adding an odorant to a fuel cell fuel supply infrastructure (fuel storage, distribution, and delivery). In one embodiment, the present invention provides an odorant composition that enables leak detection to improve safety during the transport, dispensing and use of any specialty gases that could pose any danger to humans.

A leak in a fuel cell fuel supply system includes any loss of containment of the fuel in the fuel supply system (other than a normal flow to a fuel cell). Further, the organic molecules may include elements or compounds that are consumable or at least partially consumable by the fuel cell. That is, the organic molecules may react at the fuel cell anode to provide more electricity as part of the normal fuel cell operation. Accordingly, the organic molecules may change to the degree that they do not emit a detectable odor after forming products that exhaust from the fuel cell system. Further, it should be noted that the odorant should be non-toxic, or at least has a detectable odor below toxicity levels.

The hydrogen fuel cell is a promising future power source due to its high-energy efficiency and zero emission potential. Hydrogen's potential use in fuel and energy applications includes powering vehicles, running turbines or fuel cells to produce electricity, and generating heat and electricity for buildings. The use of hydrogen as a fuel and energy carrier will require an infrastructure for safe and cost-effective hydrogen transport and storage. Some automobile manufacturers have developed hydrogen-powered vehicles, however the market for these vehicles is limited by the lack of hydrogen infrastructure. Commercial application of hydrogen fuel cells in the automotive industry will be an important driver of the hydrogen economy.

In the past, hydrogen detection has primarily relied on sensor technology because odorant solutions are challenging in the fuel cell infrastructure. The DOE office of vehicle technologies, safety, codes and standards subprogram considers hydrogen leak detection technology to be a key component in an inherently safe systems design for hydrogen applications. Several sensor technologies have been developed to detect hydrogen, including deployed systems to detect leaks in the Space Shuttle and hydrogen safety sensors for laboratory and industrial usage. The most common technologies are based on catalytic bead combustible gas sensors, infrared absorption, electrochemical oxidation of hydrogen, or the resistance/capacitance change of Pd-based materials. Considering all potential technologies for hydrogen sensing, some have excellent sensitivity while others have excellent dynamic range, and still others are too expensive or are too slow to respond. Hence, no single hydrogen sensor technology appears to exist that may meet the leak detection and safety features that will be required for the widespread use of hydrogen. Also, there appears to be no sensor that may independently provide the safety features required for all hydrogen applications.

Hydrogen fuel cells use platinum to electrochemically oxidize hydrogen at the anode of the cell. If the platinum's active sites are occupied by a molecule other than hydrogen, the activity of the catalyst, and hence the efficiency and performance of the fuel cell, dramatically decreases. This is referred to as "poisoning of the catalyst". Similarly, on-board solid-state storage devices, such as metal hydrides, carbon nanotubes, or glass microspheres may be "poisoned".

Although the odorants have been primarily described above for use in hydrogen fuel supply systems and in hydrogen fuel cells, the odorants of the present invention may be used for any fuel cell system and for other types of gases such as natural gas, blends of natural gas and hydrogen (Hythane®), LPG, propane, etc. The odorants may also be mixed with gases that are used for other purposes than as a fuel such as carrier gases, process gases, gasses used in manufacturing, gasses used as accelerants, cooling agents, conditioners, heat transfer agents, etc.

Hythane® is a mixture of natural gas and hydrogen, usually 5-7 percent hydrogen but is also common at blends of 20% hydrogen and 80% natural gas by volume. While blends of hydrogen and natural gas can be blended at any ration, vehicles or combustors that operate on blends of 20% hydrogen and 80% natural gas by volume, produce significantly lower emissions than those operating on diesel or natural gas. Natural gas is generally about 90+% methane, along with small amounts of ethane, propane, higher hydrocarbons, and "inerts" like carbon dioxide or nitrogen. Hydrogen and methane are complimentary vehicle fuels in many ways. Methane has a relatively narrow flammability range that limits the fuel efficiency and oxides of nitrogen (NOx) emissions improvements that are possible at lean air/fuel ratios. The addition of even a small amount of hydrogen, however, extends the lean flammability range significantly. Methane has a slow flame speed, especially in lean air/fuel mixtures, while hydrogen has a flame speed about eight times faster. Methane is a fairly stable molecule that can be difficult to ignite, but hydrogen has an ignition energy requirement about 25 times lower than methane and provides for enhanced ignitability. Finally, methane can be difficult to completely combust in the engine or catalyze in exhaust after treatment systems. In contrast, hydrogen is a powerful combustion stimulant for accelerating the methane combustion within an engine or combustor, and hydrogen is also a powerful reducing agent for efficient catalysis at lower exhaust temperatures.

In general odorants are currently added to natural gas and liquefied natural gas. The present invention provides odorant compositions to be added to hydrogen fuel to make a hydrogen composition. Such hydrogen composition (odorant+hydrogen) may be blended with odorized or de-odorized natural gas to provide a new alternative fuel blend composition (odorized hydrogen and natural gas) that enables both a distinctive smell of such new fuel blend composition and allows for improved environmental performance and combustion properties. The present invention provides odorants to be added to hydrogen and blended with natural gas to collectively provide for a fuel composition with a unique odor for fuel leak detection and improved combustion properties and environmental performance.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A composition comprising:
    hydrogen gas; and
    an oxygenate odorant;
    wherein the oxygenate odorant has a vapor pressure of about 0.002 psi or greater at 25° C. and 1 atm;
    wherein the oxygenate odorant has a smell detectable at less than 1 ppm by a human nose;
    wherein the oxygenate odorant includes one or more carbonyl groups;
    wherein the oxygenate odorant consists only of carbon, hydrogen and oxygen;
    wherein the oxygenate odorant is a cyclic compound; and
    wherein the oxygenate odorant is stable under the high pressure and temperature storage and use conditions required for fuel cells.

2. The composition of claim 1, wherein the oxygenate odorant has a vapor pressure in the range from about 0.002 psi to about 12 psi at 25° C. and 1 atm.

3. The composition of claim 1, wherein the oxygenate odorant has a vapor pressure greater than 0.5 psi at 25° C. and 1 atm.

4. The composition of claim 1, wherein the oxygenate odorant includes a six-membered ring.

5. The composition of claim 2, wherein the oxygenate odorant is a pyrone.

6. The composition of claim 2, wherein the oxygenate odorant is a monounsaturated pyranone.

7. The composition of claim 2, wherein the oxygenate odorant is a saturated pyranone.

8. The composition of claim 2, wherein the oxygenate odorant is a cyclohexenone.

9. The composition of claim 2, wherein the oxygenate odorant is a cyclohexanone.

10. The composition of claim 2, wherein the oxygenate odorant is a cyclohexyl ketone.

11. The composition of claim 2, wherein the oxygenate odorant is a 1-cyclohexenyl ketone.

12. The composition of claim 1, wherein the oxygenate odorant includes a five-membered ring.

13. The composition of claim 12, wherein the oxygenate odorant is a furanone.

14. The composition of claim 12, wherein the oxygenate odorant is a butyrolactone.

15. The composition of claim 12, wherein the oxygenate odorant is a cyclopentenone.

16. The composition of claim 12, wherein the oxygenate odorant is a cyclopentanone.

17. The composition of claim 12, wherein the oxygenate odorant is a 1-cyclopentenyl ketone.

18. The composition of claim 1, wherein the oxygenate odorant is an aldehyde.

19. The composition of claim 18, wherein the oxygenate odorant includes a six-membered ring.

20. The composition of claim 19, wherein the oxygenate odorant is a cyclohexyl carboxaldehyde compound.

21. The composition of claim 19, wherein the oxygenate odorant is a cyclohexene -1 -carboxaldehyde compound.

22. The composition of claim 18, wherein the oxygenate odorant includes a five-membered ring.

23. The composition of claim 22, wherein the oxygenate odorant is a cyclopentyl carboxaldehyde compound.

24. The composition of claim 1, wherein the composition consists essentially of hydrogen gas and the odorant.

25. The composition of claim 1, wherein the odorant comprises 0.01 to 1000 ppm of the composition.

26. The composition of claim 1, wherein the odorant comprises 0.1 to 40 ppm of the composition.

27. The composition of claim 1, wherein the oxygenate odorant is not harmful to humans.

28. The composition of claim 1, wherein the oxygenate odorant has a minimum olfactory power of 7.0, a minimum diffusivity of 0.02 $cm^2/s$, and a maximum molecular weight of 200g/mol.

29. The composition of claim 1, wherein the oxygenate odorant is in a vapor phase at a pressure greater than ambient pressure.

30. The composition of claim 1,
wherein the composition comprises a mixture of two or more odorants including the oxygenate odorant;
wherein the mixture of odorants has a combined vapor pressure of about 0.002 psi or greater at 25° C. and having a smell detectable at less than 1 ppm by a human nose, and
wherein the mixture of oxygenate odorants is stable under the high pressure and temperature storage and use conditions required for fuel cells.

31. The composition of claim 30, wherein two or more of the odorants are each an oxygenate odorant;
wherein each oxygenate odorant has a vapor pressure of about 0.002 psi or greater at 25° C. and 1 atm;
wherein each oxygenate odorant has a smell detectable at less than 1 ppm by a human nose;
wherein each oxygenate odorant includes one or more carbonyl groups;
wherein each oxygenate odorant consists only of carbon, hydrogen and oxygen, and
wherein each oxygenate odorant is stable under the high pressure and temperature storage and use conditions required for fuel cells.

32. The composition of claim 30, wherein one of the odorants in the mixture of odorants is a selenium compound.

33. The composition of claim 1, further comprising methane or natural gas.

34. A container containing the composition of claim 1.

35. The container of claim 34, wherein the container is part of a fuel dispensing apparatus.

36. The container of claim 34, wherein the container is connected to a fuel dispensing apparatus.

37. The container of claim 34, wherein the container is a fuel cell.

38. The container of claim 34, wherein the container is part of a vehicle.

39. The container of claim 38, wherein the vehicle includes a fuel cell.

40. The container of claim 34, wherein the container is a combustor.

* * * * *